United States Patent [19]
Lewis et al.

[11] Patent Number: 5,570,845
[45] Date of Patent: Nov. 5, 1996

[54] WASTE TREATMENT APPARATUS AND METHOD

[75] Inventors: Robert W. Lewis, Charlotte, N.C.; Randall G. McKee; William Jones, both of Lebanon, Ind.

[73] Assignee: Sterile Technology Industries, Inc., West Chester, Pa.

[21] Appl. No.: 511,027

[22] Filed: Aug. 3, 1995

[51] Int. Cl.$^6$ .................................................. B02C 19/12
[52] U.S. Cl. ........................... 241/21; 241/23; 241/24.11; 241/33; 241/65; 241/606; 422/27
[58] Field of Search ........................... 241/DIG. 38, 606, 241/65, 33, 23, 29, 159, 24.11, 21; 422/26, 27, 28, 32, 22

[56] References Cited

U.S. PATENT DOCUMENTS

| | | | |
|---|---|---|---|
| 2,708,074 | 12/1952 | Hoskins . | |
| 2,731,208 | 1/1956 | Dodd | 241/606 X |
| 4,578,185 | 3/1986 | Wilson et al. | 241/606 X |
| 4,670,227 | 6/1987 | Smith . | |
| 4,884,756 | 12/1989 | Pearson | 241/606 X |
| 5,048,766 | 9/1991 | Gaylor et al. | 241/606 X |
| 5,087,420 | 2/1992 | Jackson . | |
| 5,089,228 | 2/1992 | Meijer . | |
| 5,277,136 | 1/1994 | Davis . | |
| 5,346,142 | 9/1994 | Miller et al. | 241/606 X |
| 5,360,594 | 11/1994 | Meijer . | |
| 5,362,443 | 11/1994 | Tanaka et al. | 241/606 X |
| 5,364,589 | 11/1994 | Buehler et al. . | |
| 5,384,092 | 1/1995 | Sawhill et al. . | |
| 5,389,347 | 2/1995 | Hall | 241/606 X |

OTHER PUBLICATIONS

Description Sheet Vincent Horizontal Press, date unknown.
"Steam Sterilization for Infectious Waste Management", GTH Roland North America, Inc., date unknown.
"Infectious Waste Processor Model IWP-1000", Mediclean Technology, Inc., date unknown.
"San-I-Pak", San-I-Pak Incorporated, date unknown.
ABB Sanitec "Microlook", date unknown.

*Primary Examiner*—Mark Rosenbaum
*Attorney, Agent, or Firm*—Howson and Howson

[57] ABSTRACT

Containerized medical waste is treated by a process in which the materials are carried by a conveyor under a negative pressure to a multiple-stage shredder. Sodium hypochlorite is added at several points in the shredder section of the apparatus. The output of the shredder is compressed and the liquid component which is separated out is recirculated. The compressed solid is conveyed through a conveyor in which the temperature is maintained at a level just under 212° F. by the introduction of steam. The pressure is maintained at or below atmospheric pressure at all points in the system to prevent release of contaminated materials into the atmosphere. By using the combination of sodium hypochlorite and steam, it is possible to eliminate live microorganisms entirely while still taking advantage of low pressure to avoid accidental release of contaminated materials. Heating by steam takes place in a conveyor which is controlled by temperature sensors so that it moves only when its temperature reaches a predetermined level, e.g. 205° F. The intake conveyor is also controlled so that it does not feed waste into the treatment apparatus unless the temperature in the steam conveyor is at least at a predetermined minimum level.

21 Claims, 3 Drawing Sheets

5,570,845

WASTE TREATMENT APPARATUS AND METHOD

SUMMARY OF THE INVENTION

This invention relates generally to waste treatment, and more particularly to a method and apparatus for the treatment of infectious waste materials such as hospital waste.

A waste treatment apparatus of the kind to which this invention relates is typically located on site at a hospital or other medical facility. All potentially infectious waste material produced in the operations of the facility is treated in the waste treatment apparatus, which delivers a product which can be held safely in conventional trash containers, and transported in conventional trash trucks for disposal in landfills or similar facilities.

In the treatment of infectious waste for disposal, it is important to insure that the ultimate waste product which is to be discarded is free of pathogenic microorganisms. It is also highly desirable, and in some instances required by law, to render the waste material in a condition such that individual components, such as disposable syringes, bandages, body fluid receptacles, and even body parts removed in surgery or in autopsies, are unrecognizable.

In the past, medical waste was usually incinerated. However, environmental regulations have severely limited the use of incineration for medical waste disposal. Alternative methods, including steam autoclaving and chemical treatment have been used. Some of these methods are less than entirely effective in destroying pathogenic organisms. Others, which are effective, tend to be expensive to install and both expensive and difficult to operate. Another problem encountered in the operation of medical waste treatment systems is that sometimes odors and dangerous gases, liquids and solid particles are exhausted to the atmosphere or discharged to sanitary sewage ducts. The latter problem is particularly acute in a waste treatment apparatus employing steam autoclaving, because the steam pressure will tend to cause dangerous matter to be exhausted to the atmosphere in the event of a leak.

The principal object of this invention is to provide a treatment system for infectious waste, which assures complete destruction of pathogenic microorganisms and renders the waste materials unrecognizable, and which is an improvement over prior systems in one or more of the following respects: equipment cost; cost of operation; throughput capacity; safety; reliability; simplicity; ease of use; and environmental safety.

A preferred waste treatment apparatus in accordance with the invention comprises a conveyor, for transporting containers of waste through a tunnel having an inlet end and an outlet end; an air filter; means for drawing air out of the tunnel and forcing the air drawn out of the tunnel through the air filter, whereby air is drawn into the tunnel at least through the inlet end; shredding means arranged to receive containers of waste exiting from the outlet end of the tunnel and delivering shredded waste; means for applying a disinfectant solution to the waste as it is being shredded by the shredding means; and means for exposing the shredded waste material delivered by the shredding means to an elevated temperature for a time sufficient to effect substantially complete elimination of live microorganisms in the shredded waste material.

Another preferred waste treatment apparatus in accordance with the invention includes press means for receiving shredded waste from the shredding means, extracting liquid from the shredded waste and delivering a solid waste material; and means for recirculating liquid extracted by the press means to the shredder.

Preferably, disinfectant solution is applied to the containers before they are shredded, and again at one or more points in the shredding apparatus.

The invention also comprises a waste treatment process in which containers of waste material are transported through a tunnel; air is drawn out of the tunnel and forced through an air filter; the waste material in the containers is shredded after the containers are transported through the tunnel; a disinfectant solution is applied to the waste as it is being shredded; and, after shredding, the shredded waste material delivered by the shredding means is exposed to an elevated temperature for a time sufficient to effect substantially complete elimination of live microorganisms.

Preferably, liquid is extracted from the shredded waste material to produce a solid shredded waste material, and the solid shredded waste material is then exposed to the elevated temperature. The extracted liquid is combined with fresh disinfectant solution and recirculated through the waste.

Another feature of the invention is a control whereby waste material is prevented from being transported to the heat treating stage until the heat treating stage has reached a predetermined minimum temperature level.

Other objects, details and advantages of the invention will be apparent from the following detailed description when read in conjunction with the drawings.

DETAILED DESCRIPTION

Figure 1:
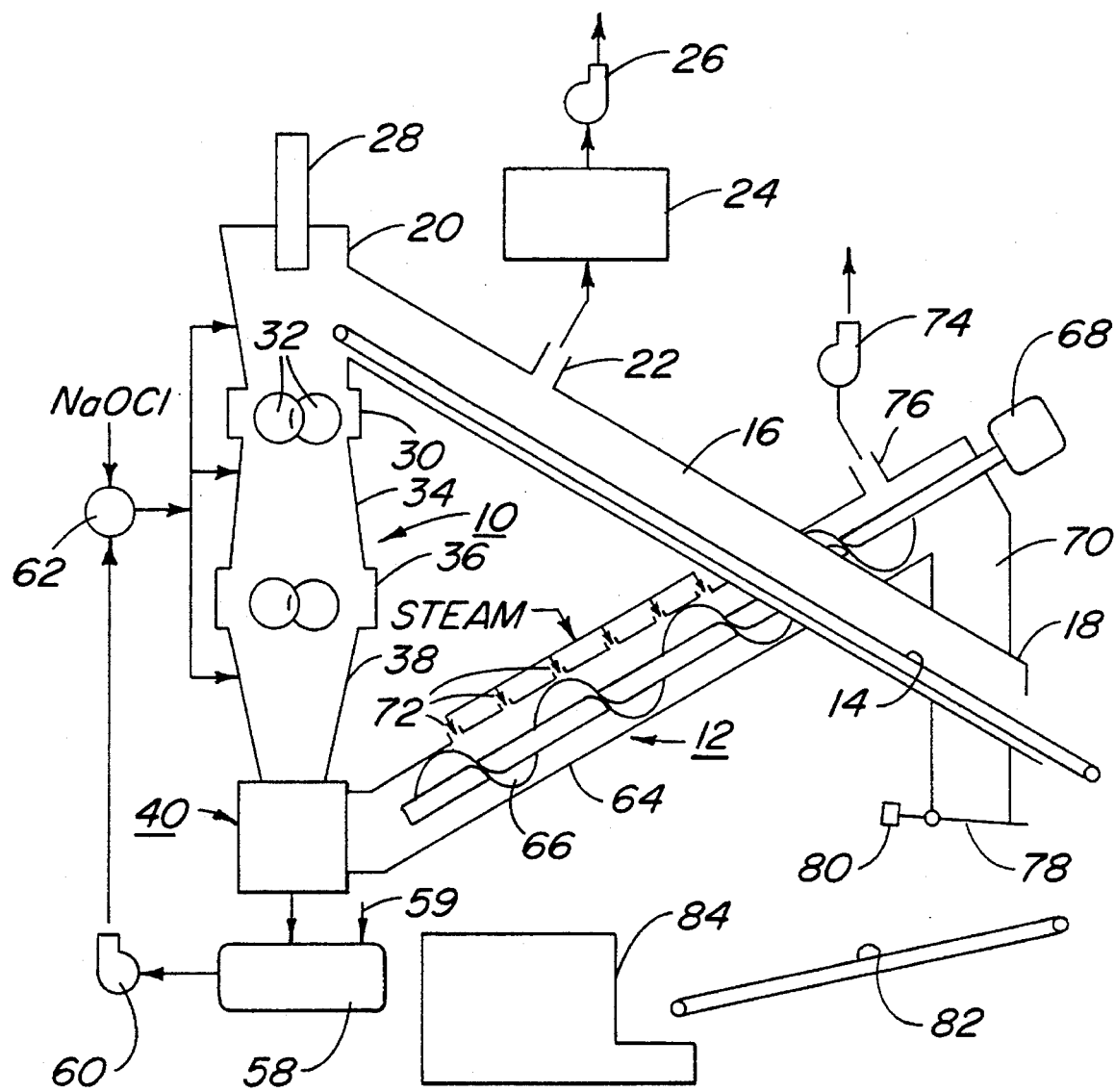
FIG. 1 is a schematic diagram of a waste treatment apparatus in accordance with the invention.

The apparatus of the invention comprises two principal components: a shredding or comminution apparatus with chemical treatment, and a heating chamber through which chemically treated waste is conveyed slowly while being subjected to heating by low pressure steam. This heating chamber will be referred to herein as a "steam conveyor." These components are illustrated in FIG. 1, in which a multi-stage shredder/chemical treatment apparatus 10 is shown delivering shredded waste to a steam conveyor 12.

A belt conveyor 14 extends through a tunnel 16, and receives containerized waste placed on the conveyor just outside the inlet end 18 of the tunnel. The conveyor carries the containers to a hopper 20 at the top of the multi-stage shredder/chemical treatment apparatus.

The tunnel 16 of steam conveyor 12 has an opening at its inlet end 18, but is otherwise essentially closed, except that it has an opening 22. Air, along with gases and particulate matter which accompany the waste material or are generated by the waste material in the initial stages of the treatment process, are exhausted through opening 22 and through a high-efficiency particulate air (HEPA) filter 24 and a blower 36. The hopper is enclosed, as is the connection between the tunnel and the hopper. Consequently, air is drawn in through opening at the inlet end of the tunnel and a negative pressure is maintained in the tunnel so that gases and particulate matter leave from the tunnel only through opening 22 or through the hopper.

The particulate filter 24 is preferably a high efficiency filter designed to remove at least 99.97% of particles having a size of 0.3 microns.

A pneumatically operated ram 28 applies downward pressure to containers as they fall into the hopper from the upper end of the belt conveyor 14. This insures that the containers are fed to a primary shredder stage 30 underneath the hopper. The primary shredder stage utilizes cooperating rotating cutters 32, which shred the containers and deliver shredded waste to a transition passage 34. Below the transition passage 34 is a secondary shredder 36 which effects a further size reduction of the waste material. The secondary shredder delivers the waste material through another transition passage 38 to a screw press 40, which is used to remove liquid from the waste material.

The shredder/chemical treatment apparatus 10 is also enclosed, and the blower 26 maintains a negative pressure in the shredder/chemical treatment apparatus as well as in the intake conveyor tunnel 16.

Figure 2:
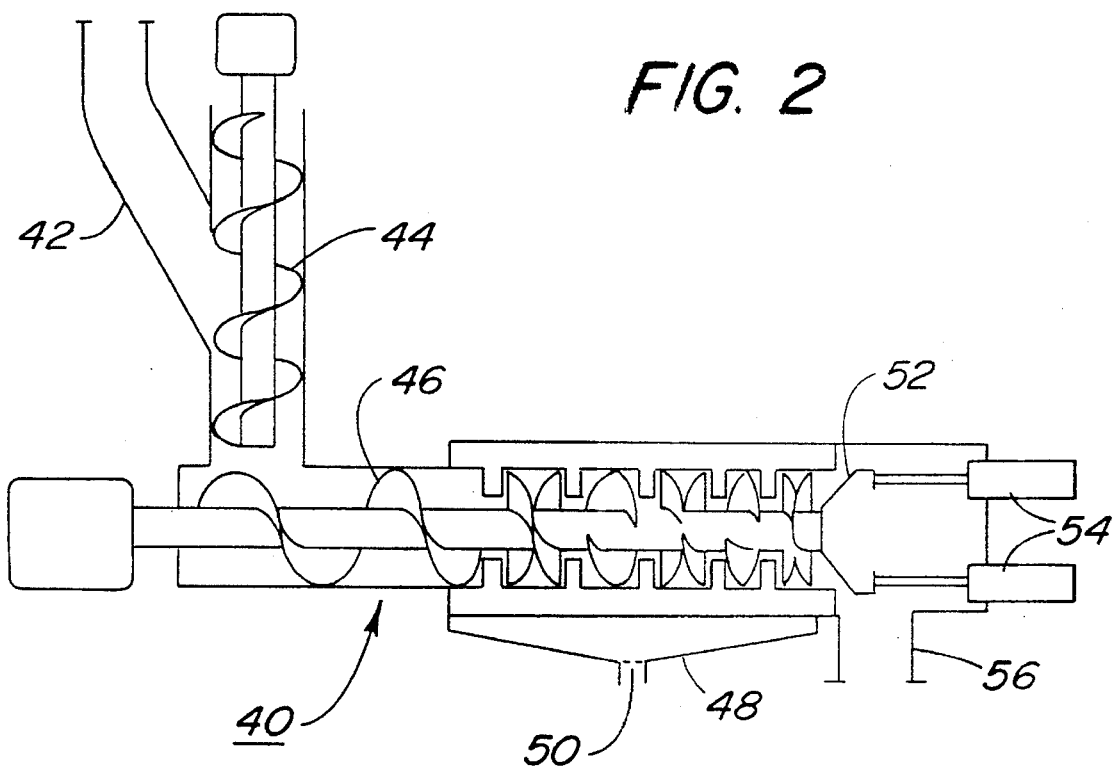
FIG. 2 is a schematic diagram showing a dewatering press which is a component of the apparatus of FIG. 1.

The screw press 40, which is also shown in FIG. 2, is preferably a horizontal dewatering press of the type available from Vincent Corporation of Tampa, Fla. The Vincent press is a continuously operating press having a screw with a graduated pitch and interrupted flights. As shown in FIG. 2, the press has an intake passage 42, and an optional vertical, motor-driven screw conveyor 44, which serves as a charging conveyor, delivers material from the intake passage to a horizontal, motor-driven screw 46. The material is gradually compressed as it is moved by screw 46, and liquid is pressed out of the material through a screen surrounding the screw and collected in a trough 48 having a drain 50. A cone 52, which can be moved axially by pneumatic cylinders 54, maintains pressure against the solid material being fed by the screw 46. Solid material moves past the cone 52 and is removed as a press cake through outlet 56 as the screw rotates. The amount of liquid extracted from the waste in the screw press can be adjusted by controlling the pressure applied to the material in the screw press by the cone 52. Various alternative dewatering presses can be used in place of the apparatus shown in FIG. 2.

Returning to FIG. 1, a disinfectant, preferably a solution of sodium hypochlorite (NaOCl), is applied to the waste material in the shredder/chemical treatment stage 10, by injecting it through spray nozzles (not shown). In the preferred embodiment of the invention, sodium hypochlorite is sprayed onto the waste containers in the hopper, before they are broken up by the shredders, and is also introduced in each of the transition passages 34 and 38. The injection of sodium hypochlorite at multiple points insures effective elimination of live microorganisms with a minimum amount of chemical and in a minimum amount of time.

To make the most efficient use of the disinfectant, the liquid separated out from the solid waste by the screw press 40 is collected in a recirculation tank 58 and pumped by a pump 60 to a mixing valve 62, where it is combined with fresh disinfectant and introduced into the shredder/chemical treatment apparatus 10. Make-up water is introduced into the recirculation tank 58 through port 59. Preferably, the mixture of fresh disinfectant and recirculated liquid is controlled so that the concentration of sodium hypochlorite in the liquid delivered by the mixing valve is in the range of 0.1% to 0.2% by weight.

The residence time of the waste in the shredder/chemical treatment apparatus should be at least three minutes, and is preferably about ten minutes.

The solid component of the waste material, taken from screw press 40 in the form of a press cake, is delivered to the intake end of the steam conveyor 12. The steam conveyor 12 comprises an elongated channel defined by a cylindrical housing 64 extending obliquely upward from the outlet of the screw press 40. A screw or auger 66, driven by a motor 68 carries the solid waste material upward through housing 64 to a discharge chute 70, which is seen extending downwardly, behind the inlet end of conveyor tunnel 16.

Steam is introduced under a low pressure, preferably not more than 15 p.s.i., into housing 64 through a series of steam inlet ports disposed at intervals along the length of the housing, and a blower 74 draws air, water vapor, and other gases through port 76 and exhausts them to the atmosphere. Port 74 is near the upper end of housing 76 so that the material has been completely treated both by the sodium hypochlorite, and by steam when it reaches the location of port 76.

A flapper valve 78, having a counterweight 80, is provided at the lower end of chute 70. This valve normally holds the discharge end of the chute closed so that the blower 74 can draw gas and vapor out through port 74. It opens under the weight of treated waste discharged from the steam conveyor 12, and prevents pressure from building up in the tunnel 16 especially in the event of failure of blower 74.

Treated waste material discharged from chute 70 through the flapper valve 78 is dropped onto conveyor 82 and carried to a compactor 84, from which compacted, treated waste can be transported safely to a landfill or to any other suitable disposal site.

In the steam conveyor 12, waste material, which has already been shredded and chemically treated with a disinfectant, is slowly mixed while being simultaneously heated by steam. The mixing insures that the disinfectant comes into complete contact with all of the waste material, and the heating insures that infectious microorganisms are killed completely.

The screw conveyor operates at a speed such that the residence time of the waste material is at least 30 minutes. In typical operation, the screw speed is adjusted so that the residence time is in the range of 30 to 45 minutes. The steam temperature should be maintained below 212° F., preferably in the range of approximately 205° to 210° F., and ideally in the range of 205° F. to 208° F. Temperature sensors in the screw conveyor are connected to controls which prevent the belt conveyor 14 from operating unless the temperature within the screw conveyor housing is at least 205°.

Figure 3:
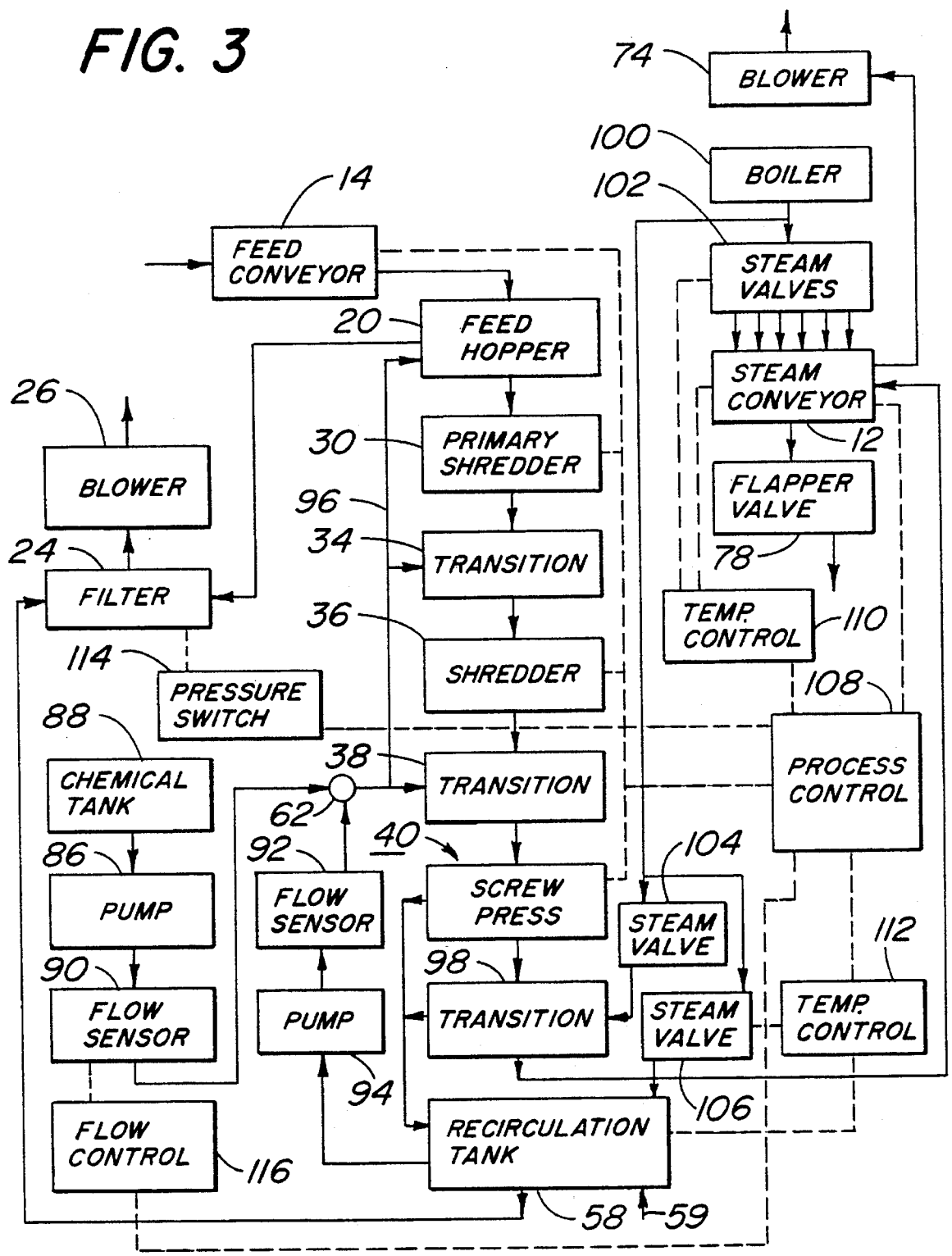
FIG. 3 is a block diagram illustrating the processing of waste in accordance with the invention.

FIG. 3 shows, in block diagram form, the sequence of treatment of the raw waste through the feed conveyor 14, the hopper 20, shredder 30, transition 34, shredder 36, transition 38 and screw press 40. Disinfectant solution, preferably a solution of sodium hypochlorite, is fed by pump 86 from a chemical tank 88, through a flow sensor 90, to mixing valve 62, where the solution is mixed with liquid recirculated from tank 58 through flow sensor 92 by pump 94. The mixture of fresh disinfectant solution with recirculated liquid, which also contains a significant quantity of usable disinfectant, is delivered through line 96, from which it is sprayed onto the waste material as it is being treated in the shredding section of the apparatus. Preferably, the mixture in line 96 is applied to the waste material at several stages in the process, including a point in the feed hopper in which the containers are sprayed with disinfectant before being shredded. Applying the disinfectant solution at several points in the shredding process provides more effective reduction in live microorganisms using smaller quantities of disinfectant.

Furthermore, the application of disinfectant to the unopened containers in the feed hopper helps guard against the escape of dangerous microorganisms in the reverse direction along the path by which waste material is fed into the apparatus.

The liquid in recirculation tank 58 is derived from the drain of the screw press 40 as well as from the transition passage 98 between the screw press and the steam conveyor 12.

Steam is produced by a boiler 100, which delivers steam under low pressure (preferably not more than 15 p.s.i.) to a set of steam valves 102. These steam valves regulate the flow of steam to inlet ports 72 (see FIG. 1) spaced along the length of the stem conveyor. The boiler also delivers steam, through a steam valve 104, to transition 98 so that the steam begins to heat the waste as it passes from the shredder/chemical treatment apparatus to the steam conveyor. Steam is also delivered from the boiler to the recirculation tank through a steam valve 106. This causes heating of the recirculated liquid, raising the temperature of the waste as it is being treated in the shredder/chemical treatment apparatus.

A process control 108, which may be a conventional, microprocessor-based chemical process controller, regulates the operation of the entire system. The most important functions of the process control are illustrated by the broken lines in FIG. 3. In particular, the temperature of the steam in the steam valves 102 and the steam conveyor 12 are sensed by thermocouples (not shown) which provide signals to temperature control 110. Likewise, the temperature of the steam in the steam valve 106 and the recirculation tank 58 is sensed by thermocouples (not shown) which provide signals to temperature control 112. The process control 108 responds to signals from the temperature controls and regulates the operation of the intake belt conveyor 14. The process control prevents the intake conveyor 14 from transporting raw waste into the apparatus unless the steam temperature is at least at the required minimum temperature (205° F.). It also halts the operation of the shredders 30 and 36 and the screw press 40 until the temperature in the steam conveyor reaches the required level.

The process controller also optionally stops the rotation of the steam conveyor screw until the steam temperature in the steam conveyor reaches the required minimum temperature. In any event, the screw in the steam conveyor rotates at a rate such that the residence time of the shredded waste in the steam conveyor is at least 30 minutes, even if the temperature within the steam conveyor stays at or above the required minimum temperature.

The process control also shuts down the operation of the feed conveyor 14 if pressure switch 114 indicates that the filter element in filter 24 needs to be replaced. The process controller 108 also senses the flow of disinfectant by a signal from flow control 116, which is associated with flow sensor 90. Here again, the process control shuts down the operation of the feed conveyor 14 in the event of insufficient flow of fresh disinfectant to mixing valve 62.

The process control 108 also shuts down the feed conveyor, shredders and screw press if a jammed condition is sensed at a downstream location in the system.

Under typical operating conditions, the retention time of waste in the shredding/chemical treatment apparatus is 10 minutes and the temperature is maintained within the 100°–110° F. range. A temperature of at least 100° F. is desirable for optimum efficacy of the sodium hypochlorite disinfectant. In the steam conveyor, the temperature is maintained in the 205°–210° F. range and preferably in the 205°–208° F. range. The residence time is 30 minutes. Sterility test indicate that, under the above conditions the process described above is capable of total elimination of live microorganisms, so that the treated waste can be safely discharged to a landfill or similar waste facility.

By maintaining the temperature in the steam conveyor at a level less than 212° F., it is possible to maintain a negative pressure in the system, and to avoid a pressure build-up which could cause leakage of noxious or dangerous gases, liquids and particulates into the environment. With the steam conveyor under a negative pressure as a result of the operation of blower 74, and with the intake conveyor and shredder/chemical treatment apparatus also under negative pressure as a result of the operation of blower 26, the entire system is maintained under negative pressure, and the escape of noxious or hazardous materials is avoided.

Various modifications can be made to the apparatus described. For example, the second shredder stage (shredder 36) is optional, and can be eliminated for certain types of waste material requiring only coarse shredding. Likewise, the charging conveyor 44 in the screw press can be eliminated. Although sodium hypochlorite is preferred as a disinfectant, various other disinfectants can be used. Still other modifications may be made to the apparatus and method described above without departing from the scope of the invention as defined in the following claims.

We claim:

1. Waste treatment apparatus comprising:

means for substantially continuously transporting waste in a path successively through first and second treatment stages, the first treatment stage comprising shredding means arranged to receive containers of waste and delivering shredded waste material, and means for applying a disinfectant solution to the waste material as it is being shredded by the shredding means; and the second treatment stage comprising means, having a plurality of steam ports arranged to direct steam toward the shredded waste material, for bringing steam into contact with the shredded waste material delivered by the shredding means and thereby exposing the shredded waste material to an elevated temperature of at least approximately 205° F. but less than 212° F., as the waste material is being transported substantially continuously, for at least approximately thirty minutes;

whereby substantially complete elimination of live microorganisms in the shredded waste material is effected.

2. Waste treatment apparatus according to claim 1 in which the means for bringing steam into contact with the shredded waste material comprises means for enclosing the shredded waste material, and conveyor means for conveying the shredded waste material through the enclosing means, and in which the conveyor means comprises auger means for mixing the shredded waste material as it is conveyed through the enclosing means.

3. Waste treatment apparatus according to claim 1 in which the means for bringing steam into contact with the shredded waste material comprises means for enclosing the shredded waste material, means for drawing gases from the enclosing means, and introduces steam into the enclosing means at a pressure such that pressure in said enclosing means remains at a level not greater than the pressure of the surrounding atmosphere.

4. Waste treatment apparatus according to claim 3 in which the means for bringing steam into contact with the shredded waste material comprises means for sensing a temperature within said enclosing means, and means, responsive to the temperature-sensing means, for controlling the residence time of the solid waste material in said enclosing means whereby the solid waste material is exposed to a temperature of at least approximately 205° for at least approximately thirty minutes.

5. Waste treatment apparatus according to claim 3 in which the means for bringing steam into contact with the shredded waste material comprises conveyor means for carrying the shredded waste material through the enclosing means, means for sensing a temperature within said enclosing means, and means, responsive to the temperature-sensing means, for controlling the movement of the conveyor means in said enclosing means whereby the solid waste material is exposed to a temperature of at least approximately 205° for at least approximately thirty minutes.

6. Waste treatment apparatus according to claim 3 in which the enclosing means has an exit through which shredded waste material is delivered after exposure to elevated temperature in the enclosing means, and including flapper means for closing the exit of the enclosing means when shredded waste material is not being delivered through the exit of the enclosing means, said flapper means being arranged to open if the pressure within the enclosing means exceeds atmospheric, whereby the pressure within said enclosing means is maintained at a level not greater than atmospheric.

7. Waste treatment apparatus comprising:
   means, comprising a conveyor, for transporting containers of waste;
   means providing a tunnel through which containers of waste travel as they are transported by the conveyor, the tunnel having an inlet end through which containers of waste enter the tunnel and an outlet end through which containers of waste exit from the tunnel;
   means for causing the conveyor to transport containers of waste through the tunnel;
   an air filter;
   means for drawing air out of the tunnel and forcing the air drawn out of the tunnel through the air filter, whereby air is drawn into the tunnel at least through the inlet end;
   shredding means arranged to receive containers of waste and delivering shredded waste material;
   means for applying a disinfectant solution to the waste material as it is being shredded by the shredding means; and
   means for exposing the shredded waste material delivered by the shredding means to an elevated temperature for a time sufficient to effect substantially complete elimination of live microorganisms in the shredded waste material;
   said apparatus including press means for receiving shredded waste from the shredding means and extracting liquid from the shredded waste and delivering a solid waste material; and means for recirculating the liquid extracted by the press means to the shredding means.

8. Waste treatment apparatus according to claim 7 in which said recirculating means delivers at least part of the extracted liquid to the containers of waste before they reach the shredding means.

9. Waste treatment apparatus according to claim 7 in which said recirculating means delivers part of the extracted liquid to the containers of waste before they reach the shredding means and also delivers a part of the extracted liquid directly to the shredded waste in the shredding means.

10. Waste treatment apparatus according to claim 7 in which said press means is a screw press.

11. Waste treatment apparatus according to claim 7 in which said press means includes means for adjustably controlling the pressure applied to the shredded waste from which liquid is being extracted.

12. Waste treatment apparatus according to claim 7 in which said means for recirculating liquid extracted by the press means to the shredder includes means for combining recirculated liquid with fresh disinfectant solution.

13. A waste treatment process comprising the steps of:
   substantially continuously transporting containers of waste material in a path successively through first and second treatment stages;
   shredding waste material as it is being transported through the first treatment stage;
   applying a disinfectant solution to the waste material as it is being shredded in the first treatment stage; and
   directing steam through a plurality of steam ports toward, and into contact with, the shredded waste material as it is being transported substantially continuously through the second treatment stage, and thereby exposing the shredded waste material to an elevated temperature of at least approximately 205° F. but less than 212° F. for at least approximately thirty minutes to effect substantially complete elimination of live microorganisms in the shredded waste material.

14. A waste treatment process according to claim 13 in which the disinfectant is an aqueous solution of sodium hypochlorite.

15. A waste treatment apparatus according to claim 13 in which the disinfectant is an aqueous solution of sodium hypochlorite at a concentration in the range of approximately 0.1% to 0.2% by weight.

16. A waste treatment process according to claim 13 in which the disinfectant is an aqueous solution of sodium hypochlorite at a concentration in the range of approximately 0.1% to 0.2% by weight, in which the step of applying a disinfectant solution is followed by the step of extracting liquid from the shredded waste material, and in which the waste material, after the initiation of shredding, and before the extraction of liquid, is exposed to the disinfectant solution for at least 3 minutes.

17. A waste treatment process according to claim 13 in which the step of applying a disinfectant solution is followed by the step of extracting an amount of liquid from the shredded waste material sufficient to leave only an active surface film of disinfectant solution on the shredded waste material.

18. A waste treatment process according to claim 13 in which the step of applying a disinfectant solution is followed by the step of extracting liquid from the shredded waste material, in which the extracted liquid is combined with fresh disinfectant solution, and the disinfectant solution applied in the step of applying a disinfectant solution to the waste is the combination of the extracted liquid and the fresh disinfectant solution.

19. A waste treatment process according to claim 18 in which the fresh disinfectant solution is an aqueous solution of sodium hypochlorite, and in which the concentration of the fresh disinfectant solution and the rate at which it is combined with the extracted liquid are such that the disinfectant solution applied to the waste contains sodium hypochlorite at a concentration in the range of approximately 0.1% to 0.2% by weight.

20. A waste treatment process according to claim 13 in which the shredded waste material is exposed to the elevated temperature for approximately 30 to 45 minutes.

21. A waste treatment process according to claim 13 in which the steps of shredding, applying disinfectant and exposing the shredded waste material to an elevated temperature are carried out at a pressure below atmospheric pressure.

\* \* \* \* \*